(12) United States Patent
Vass et al.

(10) Patent No.: US 7,973,185 B2
(45) Date of Patent: Jul. 5, 2011

(54) PROCESS FOR THE PREPARATION OF PHENOLIC HYDROXY-SUBSTITUTED COMPOUNDS

(75) Inventors: András Vass, Veszprém (HU); József Dudás, Veszprém (HU); László Borbély, Dorog (HU); Ferenc Haász, Esztergom (HU); Péter Jekkel, Esztergom-Kertváros (HU)

(73) Assignee: Richter Gedeon Nyrt., Budapest (HU)

( * ) Notice: Subject to any disclaimer, the term of this patent is extended or adjusted under 35 U.S.C. 154(b) by 1079 days.

(21) Appl. No.: 11/577,434

(22) PCT Filed: Dec. 7, 2005

(86) PCT No.: PCT/HU2005/000128
§ 371 (c)(1),
(2), (4) Date: Apr. 18, 2007

(87) PCT Pub. No.: WO2006/061666
PCT Pub. Date: Jun. 15, 2006

(65) Prior Publication Data
US 2008/0039643 A1 Feb. 14, 2008

(30) Foreign Application Priority Data

Dec. 8, 2004 (HU) .................................. 0402530
Nov. 11, 2005 (HU) .................................. 0501044

(51) Int. Cl.
*C07J 1/00* (2006.01)
(52) U.S. Cl. ........................................ 552/625
(58) Field of Classification Search ............ 552/625
See application file for complete search history.

(56) References Cited

U.S. PATENT DOCUMENTS 4,339,614 A 7/1982 Olah

OTHER PUBLICATIONS

Node, M. et al., Hard Acid and Soft Nucleophile System . . . , J. Org. Chem., 1980, vol. 45, pp. 4275-4277.

*Primary Examiner* — Barbara P Badio
(74) *Attorney, Agent, or Firm* — Jason D. Voight

(57) ABSTRACT

The invention relates to a process for the preparation of a phenolic hydroxy-substituted compound of the general formula (I) by desalkylation of an alkyl aryl ether of the general formula (II) by treatment with a thiourea/aluminum chloride reagent pair, in said general formulae $R^1$ stands for straight chain or branched $C_{1-6}$ alkyl group; $R^2$, $R^3$, $R^4$, $R^5$, and $R^6$ have the same or different meanings and stand for hydrogen or halogen atom, hydroxy, carboxy, nitro, oxo, $C_{1-6}$ alkylcarbonyl, straight chain or branched alkyl or -alkoxy, or aryl group, or $R^2$ and $R^3$ together stand for a 5-7 membered ring or fused ring system; said 5-7 membered ring may be a partially saturated ring optionally substituted with an oxo group or can be an unsaturated ring; or said fused ring system may constitute with the first ring a steroid, preferably an estratriene derivative optionally substituted with an oxo or $C_{1-6}$ alkylcarbonyloxy group in the 17 position.

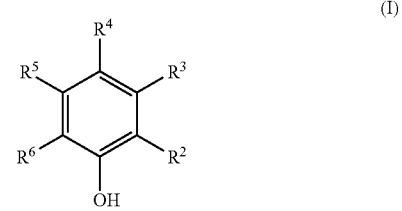

(I)

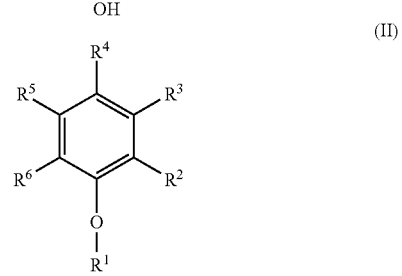

(II)

13 Claims, No Drawings

PROCESS FOR THE PREPARATION OF PHENOLIC HYDROXY-SUBSTITUTED COMPOUNDS

This is the National Stage of International Application PCT/HU2005/000128, filed Dec. 7, 2005.

The invention relates to a process for the preparation of a phenolic hydroxy-substituted compound of the general formula (I) by desalkylation of an alkyl aryl ether of the general formula (II) by treatment with a thiourea/aluminium chloride reagent pair,

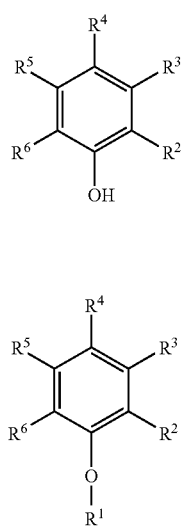

—in said general formulae $R^1$ stands for straight chain or branched $C_{1-6}$ alkyl group; $R^2$, $R^3$, $R^4$, $R^5$, and $R^6$ have the same or different meanings and stand for hydrogen or halogen atom, hydroxy, carboxy, nitro, oxo, $C_{1-6}$ alkylcarbonyl, straight chain or branched alkyl or—alkoxy, or aryl group, or $R^2$ and $R^3$ together may stand for a 5-7 membered ring or a fused ring system; said 5-7 membered ring may be a partially saturated ring optionally substituted with an oxo group or can be an unsaturated ring; or said fused ring system may constitute with the first ring a steroid, preferably an estratriene derivative optionally substituted with an oxo or $C_{1-6}$ alkylcarbonyloxy group in the 17 position.

Since the phenolic hydroxy is susceptible both to oxidation and to nucleophilic reactions, it is usually brought into temporalily protected form in the course of the synthesis. Various protective groups are known of which those protecting the hydroxy in the form of an ether, e.g. in the form of alkoxy, particularly methoxy are preferred, since these are easy-to-prepare and the protection is broad in scope. The drawback of this method, however, is that protective group can only be removed under drastic reaction conditions.

For demethylation of the alkyl aryl ethers various reactions and reagents are known of which—without the aim of completeness—those used most frequently are listed below:

Demethylation of methoxybenzene by aluminium chloride ($AlCl_3$) was described in 1944. The drawback of this method is that during the reaction poisonous methyl chloride gas developed; what is more, depending on the molar ratio of the starting material and the $AlCl_3$, the aromatic ring became methylated to different extent (Baddeley, G.: J. Chem. Soc., p. 330, 1944).

Acidic cleavage of the ether bond by hydrogen iodide (HI) (Coombs, M. M. and Roderick, H. R.: Steroids, Vol. 6, p. 841, 1965) or by boron tribromide ($BBr_3$) (Bhatt, M. V. and Kulkarni, S. U.: Synthesis, p. 249, 1983) is also known. However, corrosive properties and high prices of these reagents are against the industrial application of both processes.

The regioselective demethylation of polymethoxy benzaldehyde by aluminium chloride was studied in benzene. The use of benzene, however, makes difficult the industrial application (Paul, E. G. and Wang, P. S.-C.: J. Org. Chem., Vol. 44, p. 2307, 1979). No mention happens in this publication to demethylation of alkyl groups other than methyl, neither to the demethylation of fused ring aromatic ethers or steroids.

Demethylation by pyridine hydrochloride requires extreme reaction conditions (180-220° C.) (Groen, M. B. and Zeelen, F. J.: Tetrahedron Letters, Vol. 23, p. 3611, 1982).

Regioselective cleavage of the ether bond by aluminium iodide ($AlI_3$) in acetonitrile was described by Bhatt, M. V. and Babu, J. R. Tetrahedron Letters, Vol. 25, p. 3497, 1984, and the same effect was found by Node, M. et al when they used aluminium chloride/sodium iodide reagent pair (Chem. Pharm. Bull., Vol. 31, p. 4178, 1983).

The effect of trimethylsilyl iodide reagent [$(Me)_3SiI$] on several ethers was studied by Jung, M. E. and Lister, M. A. (J. Org. Chem., Vol. 42, p. 3761, 1977), while Winterfeldt, E. (Synthesis, p. 617, 1975) used diisobutylaluminium hydride reagent (DIBAH) in his experiments.

Stein, R. P. et al used methylmagnesium iodide (MeMgI) for the demethylation of acid sensitive steroids (Tetrahedron, Vol. 26, p 1917 (1970)), while Wunderwaldt, M. et al demethylated 3-methoxyestra-1,3,5(10)-triene derivatives substituted on the D-ring by treatment with a potassium-tert-butoxide/ethanethiol ($KOCMe_3$/EtSH) reagent pair (Z. Chem., Vol. 21, p. 145, 1981). In the latter case hexamethylphoshorous triamide (HMPT) was used as solvent.

An interesting reagent pair, i.e. a 2,3,11,12-dicyclohexano-1,4,7,10,13,15-hexaoxacyclooctadecane/potassium pair (or otherwise: dicyclohexano-18-crown-6/potassium) was used by Ohsawa, T. et al (Tetrahedron Letters, Vol. 33, p. 5555, 1992) to demethylate anisole-derivatives and the products were obtained with good yields.

Andre, J. D. et al demethylated opiate derivatives by using a methanesulfonic acid ($MeSO_3H$)/methionine (α-amino-γ-methyl-mercaptobutyric acid) reagent pair with success (Syn. Commun., Vol. 22. p. 2313, 1992). However, the high price of the methanesulfonic acid and that it was used in a 30-fold excess is against its industrial application.

Of the processes listed above the best yields for the ether bond cleavage could be achieved when $BBr_3$ in dichloromethane, DIBAH in toluene, as well as when $KOCMe_3$/EtSH or dicyclohexano-18-crown-6/potassium reagent pairs were used.

The processes reviewed above are common in that their plant scale realisations are not without difficulties: the reagents are expensive and the reactions require extreme conditions and/or result in poor yields.

The application of a "strong acid/weak nucleophil" reagent pair brought a break-through to the ether-desalkylation technique. In the so called Fujita-method a Lewis acid (a metal halogenide) and—as weak nucleophil—EtSH were used.

Of the reagent pairs of this type the boron trifluoride diethyl etherate, the $AlCl_3$/EtSH and the aluminium bromide ($AlBr_3$)/EtSH gave the most promising results (Node, M. et al: J. Org. Chem., Vol. 45, p. 4275, 1980). Considering the necessary reaction conditions, the safe application of the reagents and last but no least the price of the reagents, it is only the AlCl$_3$/EtSH reagent pair used in the Fujita ether cleavage process which can be realised with proper yield and at reasonable cost in plant scale. Besides the advantages, this process has several drawbacks: the AlCl$_3$/EtSH reagent pair should be used in 3-6 fold excess based on the amount of the ether to be demethylated; when the reaction is finished the excess EtSH (which is used also as a solvent for the reaction) and the ethyl methyl thioether (which presumably is formed in the reaction) should be eliminated by oxidation; the thio compounds used and formed in the reaction have low boiling points and have disagreeable odor also in low concentrations, causing additional costs to provide environmentally acceptable operation and any fault of the operation may result in air pollution.

To avoid problems arising from the penetrating odor, recently efforts have been made to improve the methods working with alkylthiol and arilthiol reagents to cleave the ether bond. According to Node's version (Node, M. et al: Tetrahedron Letters, Vol. 42, p. 9207, 2001) the penetrating EtSH could be replaced by the odorless 1-dodecanethiol (lauryl mercaptan) among others in the Fujita-method. This publication mentions only the yield, which is excellent, but no other details are given.

At the first sight the use of the 1-dodecanethiol seems attractive, but when plant scale application is considered, several questions come up. The 1-dodecanethiol is sparingly soluble in water (0.01 g in 100 g water) but is readily soluble in organic solvents, causing that during the work up of the reaction mixture with an aqueous treatment, it is contained in the same phase as the product, i.e. an additional separation step is necessary to remove it. The same applies to the 1-dodecane methyl thioether formed in the reaction. On the other hand, the 1-dodecanethiol is a surfactant (a property, inherent in its structure), which may cause difficulties in the phase separation step.

The data (reagent, solvent, temperature, time, yield and reference) of the most important reactions for the desalkylation of ethers are shown in Table 1 below.

Wherein the references are as listed below:
A/ Baddeley, G.: J. Chem. Soc., p. 330, 1944
B/ Coombs, M. M. and Roderick, H. R.: Steroids, Vol. 6, p. 841, 1965;
C/ Paul, E. G. and Wang, P. S.-C.: J. Org. Chem., Vol. 44, p. 2307, 1979
D/ Bhatt, M. V. and Kulkarni, S. U.: Synthesis, p. 249, 1983;
E/ Groen, M. B. and Zeelen, F. J.: Tetrahedron Letters, Vol. 23, p. 3611, 1982;
F/ Bhatt, M. V. and Babu, J. R.: Tetrahedron Letters, Vol. 25, p. 3497, 1984;
G/ Node, M. et al: Chem. Pharm. Bull., Vol. 31, p. 4178, 1983;
H/ Jung, M. E. and Lister, M. A.: J. Org. Chem., Vol. 42, p. 3761, 1977;
I/ Winterfeldt, E.: Synthesis, p. 617, 1975
J/ Stein, R. P. et al: Tetrahedron, Vol. 26, p. 1917, 1970;
K/ Wunderwald, M. et al: Z. Chem., Vol. 21, p. 145, 1981;
L/ Ohsawa, T. et al: Tetrahedron Letters, Vol. 33, p. 5555, 1992;
M/ Andre, J. D. et al: Syn. Commun., Vol. 22, p. 2313, 1992;
N/ Node, M. et al: J. Org. Chem., Vol. 45, p. 4275, 1980;
O/ Node, M. et al: Tetrahedron Letters, Vol. 42, p. 9207, 2

To sum up the literature data it can be said that the Fujita method is the most suitable for plant scale desalkylation of alkyl aryl ethers (item N in Table 1). This process, however, has an unquestionable disadvantage: the use of the thiol reagents with intense, disagreeable odor.

Since in the pharmaceutical industry desalkylation is a frequently used procedure and the processes listed above go with difficulties at plant scale (expensive reagents, extreme reaction conditions, low yield, intensive odor penetrating into the air), our aim is to provide a new desalkylation process without the use of alkanethiols.

Our invention is based on that we have found that thiourea and AlCl$_3$ form together a reagent pair. It is a colorless and odorless liquid with moderate viscosity which is readily soluble in certain organic solvents (e.g. in dichloromethane, 1,2-dichloroethane, chloroform, benzene, toluene, xilene) while insoluble in 1,1,2,2-tetrachloroethylene.

TABLE 1

The most important known reactions for the desalkylation of ethers

| Reagents | Solvent | Temperature (° C.) | Time (h) | Yield (%) | Reference |
|---|---|---|---|---|---|
| AlCl$_3$ | without solvent | 100 | 3 | 15-100 | A |
| HI | acetic acid/water | 100 | 0.5 | 68 | B |
| AlCl$_3$ | benzene | 50 | 7.5 | 84 | C |
| BBr$_3$ | dichloromethane, benzene, pentane | −80-+20 | 2 h-7 days | 14-93 | D |
| pyridine•HCl | — | 180-220 | 1 | 53 | E |
| AlI$_3$ | acetonitrile | 82 | 1-12 | 90-94 | F |
| AlCl$_3$/NaI | acetonitrile/dichloromethane | reflux | 5.5 | 70 | G |
| (Me)$_3$SiI | CD$_2$Cl$_2$ | 25-60 | 0.1-125 | 70-100 | H |
| DIBAH | toluene | 70-80 | — | 81-95 | I |
| MeMgI | melt | 165-170 | 3 | 90 | J |
| KOCMe$_3$/EtSH | HMPT | 150 | 2 | 96 | K |
| dicyclohexano-18-crown-6/potassium | toluene or tetrahydrofuran | 20 | 2 | 80-100 | L |
| MeSO$_3$H/methionine | MeSO$_3$H | 20-80 | 6-55 | 50-80 | M |
| AlCl$_3$/EtSH | EtSH | 0-20 | 0.5-3.5 | 70-98 | N |
| AlCl$_3$/1-dodecanethiol | 1-dodecanethiol | 20 | 1 | 77-97 | O |

Further experiments showed that the reagent pair containing the thiourea and AlCl₃ in equimolar amount can dissolve excess of AlCl₃ too (0.5-1.5 mol AlCl₃ is present as excess). This is an advantage when said reagent pair is used in a desalkylation process according to the invention; namely we have found that in the thiourea/AlCl₃ reagent pair the sulphur atom acts as a weak nucleophil and is capable of cleaving a methyl group from a methoxy, similarly to the AlCl₃/EtSH reagent.

In a pilot experiment the 17β-acetoxyestra-1,3,5,(10)-triene-3-ol of the formula (III), an intermediate used in the manufacture of pharmaceuticals was prepared

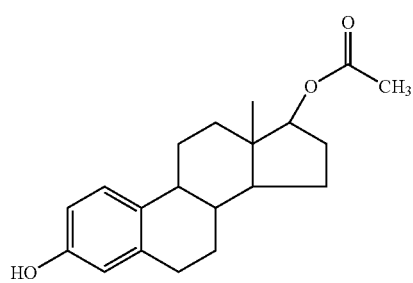
(III)

by the demethylation of 3β-methoxy-17β-acetoxyestra-1,3,5 (10)-triene of the formula (IV)

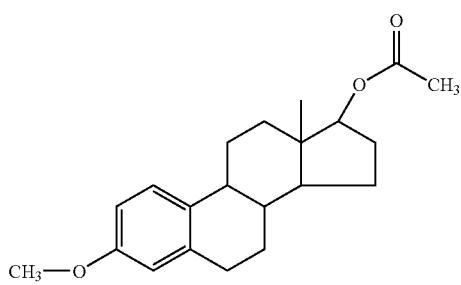
(IV)

without the use of an alkanethiol reagent.

The new process according to the invention gives 17β-acetoxiestra-1,3,5(10)triene-3-ol of the formula (III) in good yield and high purity by demethylation of 3β-methoxy-17β-acetoxyestra-1,3,5(10)-triene of the formula (IV) by treatment with the thiourea/AlCl₃ reagent pair.

Next, another steroid, the 3β-hydroxyestra-1,3,5(10)-triene-17-one of the formula (V), also an intermediate in the manufacture of pharmaceuticals was prepared,

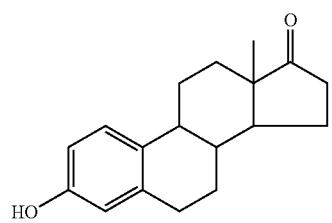
(V)

by demethylation of the 3β-methoxyestra-1,3,5(10)-triene-17-one of the formula (VI), by treatment with thiourea/AlCl₃ reagent pair.

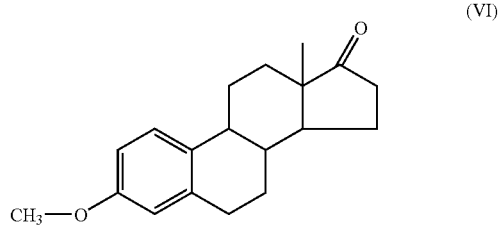
(VI)

In a study we subjected several other compounds to demethylation by using the thiourea/AlCl3 reagent pair of the invention and found that the process utilizing thiourea/AlCl₃ can be extended to the preparation of various substituted phenols and naphthols. In all the reactions studied the appropriate, phenolic hydroxy-substituted compounds were obtained and successfully recovered.

Further, we have found that these phenolic hydroxy-substituted compounds can be prepared not only by demethylation but also by desalkylation (i.e. by the removal of a $C_{1-6}$ alkyl group from the corresponding starting material) by using the thiourea/AlCl₃ reagent pair.

Thus, in our experiments we have found that the new demethylation process using the thiourea/AlCl₃ reagent pair for the preparation of 17β-acetoxyestra-1,3-5(10)-triene-3-ol of the formula (III) can be extended for the preparation of a phenolic hydroxy-substituted compound of the general formula (I) by desalkylation of an alkyl aryl ether of the general formula (II) by treatment with a thiourea/aluminium chloride reagent pair.

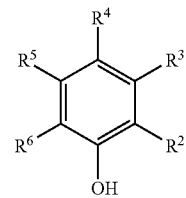
(I)

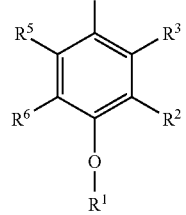
(II)

—in said general formulae $R^1$ stands for straight chain or branched $C_{1-6}$ alkyl group; $R^2$, $R^3$, $R^4$, $R^5$, and $R^6$ have the same or different meanings and stand for hydrogen or halogen atom, hydroxy, carboxy, nitro, oxo, $C_{1-6}$ alkylcarbonyl, straight chain or branched alkyl or -alkoxy, or aryl group, or $R^2$ and $R^3$ together may stand for a 5-7 membered ring or a fused ring system; said 5-7 membered ring may be a partially saturated ring optionally substituted with an oxo group or can be an unsaturated ring; or said fused ring system may constitute with the first ring a steroid, preferably an estratriene derivative optionally substituted with an oxo or $C_{1-6}$ alkylcarbonyloxy group in the 17 position.

The new process has several advantages, i.e. the products are obtained with good yields and purity; the process is easy to realize in plant scale, can be operated in an environmentally acceptable fashion in a manner not known is the art to avoid the use of substances having disagreeable odor.

We have found only one reference concerning the thiourea/AlCl$_3$ reagent pair. It's the Soviet patent application No. 603 395 (priority data: 1976. 11. 22-SU- 2421790) which discloses that burning metals, such as aluminium and magnesium can be extinguished with a "thiourea/aluminium chloride compound" prepared by mixing its components in equimolar ratio at a temperature below 50° C.; said compound is a homogenous, transparent liquid with moderate viscosity and certain physical characteristics are also given. It is also mentioned that said compound has been previously used in spectroscopy as model substance to detect the existence of chemical association.

No mention happens in the technical literature to that by using the thiourea/AlCl$_3$ reagent pair the phenolic hydroxy-substituted compounds of the general formula (I) can be prepared from the aryl alkyl ethers of the general formula (II) whereby the compound of the general formula (II) is desalkylated (or in other words: the phenolic hydroxy of the compound is liberated), nor is mentioned that the use of the thiourea/AlCl$_3$ can be advantageous in organic reactions.

Accordingly, the object of the invention is process for the preparation of a phenolic hydroxy-substituted compound of the general formula (I) by desalkylation of an alkyl aryl ether of the general formula (II) by treatment with a thiourea/aluminium chloride reagent pair,

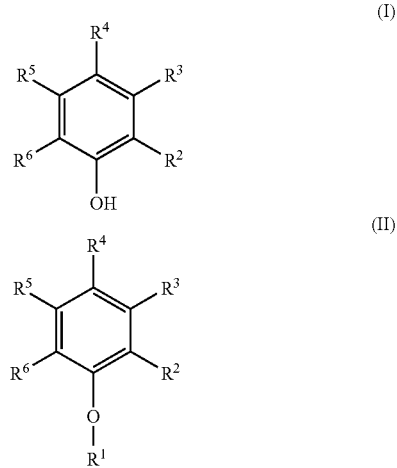

—in said general formulae R$^1$ stands for straight chain or branched C$_{1-6}$ alkyl group; R$^2$, R$^3$, R$^4$, R$^5$, and R$^6$ have the same or different meanings and stand for hydrogen or halogen atom, hydroxy, carboxy, nitro, oxo, C$_{1-6}$ alkylcarbonyl, straight chain or branched alkyl or -alkoxy, or aryl group, or R$^2$ and R$^3$ together may stand for a 5-7 membered ring or fused ring system; said 5-7 membered ring may be a partially saturated ring optionally substituted with an oxo group or can be an unsaturated ring; or said fused ring system may constitute with the first ring a steroid, preferably an estratriene derivative optionally substituted with an oxo or C$_{1-6}$ alkylcarbonyloxy group in the 17 position.

In the compounds of the general formula (II) R$^1$ may stand for straight chain or branched C$_{1-6}$ alkyl group, such as methyl, ethyl, n-propyl or n-butyl group.

In the compounds of the general formulae (I) and (II) R$^2$, R$^3$, R$^4$, R$^5$ and R$^6$ may stand for halogen atom, such as chloride, bromide, iodine or fluorine atom.

In the compounds of the general formulae (I) and (II) R$^2$, R$^3$, R$^4$, R$^5$ and R$^6$ when are defined as an alkylcarbonyl group, may mean a straight chain or branched C$_{1-6}$ alkylcarbonyl group, such as methylcarbonyl, ethylcarbonyl, n-propylcarbonyl, isopropylcarbonyl, n-butylcarbonyl, tertiarybutylcarbonyl group.

In the compounds of the general formulae (I) and (II) R$^2$, R$^3$, R$^4$, R$^5$ and R$^6$ when are defined as straight chain or branched C$_{1-6}$ alkyl group, may mean e.g. methyl, ethyl, n-propyl, isopropyl, n-butyl, tertiarybutyl group.

In the compounds of the general formulae (I) and (II) R$^2$, R$^3$, R$^4$, R$^5$ and R$^6$ when are defined as straight chain or branched C$_{1-6}$ alkoxy group, may mean e.g. methoxy, ethoxy, n-propoxy, isopropoxy, n-butoxy, tertiarybutoxy group.

In the compounds of the general formulae (I) and (II) R$^2$, R$^3$, R$^4$, R$^5$ and R$^6$ may stand for an aryl group, such as a phenyl or benzyl group.

In the compounds of the general formulae (I) and (II) R$^2$, R$^3$ together may stand for an unsaturated or a partially saturated 5-7 membered ring constituting with the original ring a fused ring system, such as naphthalene or 5,6,7,8-tetrahydronaphthalene.

When in the compounds of the general formulae (I) and (II) R$^2$, R$^3$ together may stand for a fused ring system, the fused ring system may constitute with the first ring a steroid, preferably an estratriene derivative optionally substituted with an oxo or C$_{1-6}$ alkylcarbonyloxy group in the 17 position;—said alkylcarbonyloxy is a straight or branched C$_{1-6}$ alkylcarbonyloxy, such as methylcarbonyloxy, ethylcarbonyloxy, n-propylcarbonyloxy, isopropylcarbonyloxy, n-butylcarbonyloxy, tertiarybutylcarbonyloxy. Such estratriene derivative may be e.g. the 17β-acetoxyestra-1,3,5(10)-triene-3-ol of the formula (III) or the 3β-hydroxyestra-1,3,5(10)-triene-17-one of the formula (V).

It is to be mentioned that the 17β-acetoxyestra-1,3,5(10)-triene-3-ol or by other name: estradiol-17β-acetate of the formula (III) is an early intermediate for the synthesis of estradiol (other name: estra-1,3,5(10)-triene-3,17p-diol) and ethynylestradiol (other name: 17α-ethynylestra-1,3,5(10)-triene-3,17p-diol), which are the estrogenic components of pharmaceutical compositions used for contraception and for the treatment of hormone deficiency.

The detailed description of the invention is as follows:

The term "room temperature" means a temperature ranging about from 20° C. to 25° C.

The phenolic hydroxy-substituted compounds of the general formula (I) according to the invention are prepared from the alkyl aryl ethers of the general formula (II) usually in such a manner that the thiourea in an amount of 1-3 mol equivalent per ether group is mixed with 1-6 mol equivalent of AlCl$_3$. The reaction with the careful exclusion of moisture is carried out without the use of a solvent, or in a suitable solvent, such as dichloromethane, 1,2-dichloroethane, chloroform, benzene, toluene, xilene, 1,1,2,2-tetrachloroethane, 1,1,2,2-tetrachloroethylene. The mixture is stirred for a short time at 100 rpm and then to the reagent pair formed (a liquid), 1 mol equivalent amount of the alkyl aryl ether of the general formula (II) is added.

The addition order of the reaction components is interchangeable.

The reaction mixture is heated to 40-100° C. and is maintained at this temperature for 1-3 hours. Then the mixture is cooled and 5 wt % hydrochloride acid is added. In some cases the product is simply filterable. When the product is remained in a solution, the aqueous layer is extracted by the appropriate solvent, and the organic layer so obtained is washed with alkali, 1-5 wt % sodium hydroxide, sodium carbonate or sodium bicarbonate to recover the product. The pH of the alkaline aqueous layer is adjusted to be acidic, the precipitated phenolic product is recovered by filtration or if necessary extraction followed by evaporation.

The molar ratio of the components in the thiourea/$AlCl_3$ reagent pair used in the process according to the invention is varied from 1:1 to 1:4, preferably from 1:1 to 1:2.

In the process according to the invention the thiourea component of the thiourea/$AlCl_3$ reagent pair generally is used in 1-5 mol equivalent amount, whereas the $AlCl_3$ component in 1-20 mol equivalent amount based on one ether group present in the alkyl aryl ether of the general formula (II) in question.

For the preparation of a phenolic hydroxy-substituted compound of the general formula (I) by the process according to the invention using the thiourea/$AlCl_3$ reagent pair, suitably a compound of the general formula (II) wherein $R^1$ stands for $C_{1-6}$ alkyl, preferably a methyl, ethyl, n-propyl or n-butyl is applied.

The desalkylation process using the thiourea/$AlCl_3$ reagent pair to prepare a phenolic hydroxy-substituted compound of the general formula (I) from the corresponding alkyl aryl ether of the general formula (II) can be carried out in the presence of one or more solvents or without the use of a solvent. Suitably the following solvents can be used: dichloromethane, 1,2-dichloroethane, chloroform, benzene, toluene, xilene, 1,1,2,2-tetrachloroethane, 1,1,2,2-tetrachloroethylene.

Although the thiourea/$AlCl_3$, a liquid state reagent pair, is insoluble in 1,1,2,2-tetrachloroethylene, in certain cases it is necessary to use said solvent to dissolve the alkyl aryl ether. In such a case the procedure is as follows:

The thiourea/$AlCl_3$, a liquid state reagent pair is dissolved e.g. in dichloromethane; to this solution
the alkyl aryl ether dissolved in tetrachloroethylene is added; or
first the alkyl aryl ether and subsequently the tetrachloroethylene are added.

The desalkylation process using the thiourea/$AlCl_3$ reagent pair to prepare a phenolic hydroxy-substituted compound of the general formula (I) from the corresponding alkyl aryl ether of the general formula (II) is performed at a temperature ranging suitably from 0° C. to 130° C.

By carrying out the reaction according to the invention in the presence of the thiourea/$AlCl_3$ reagent pair and organic solvents, preferably dichloromethane and 1,1,2,2-tetrachloroethylene, the 17β-acetoxyestra-1,3,5(10)-triene-3-ol (III) was successfully prepared by demethylation of 3β-methoxy-17β-acetoxyestra-1,3,5(10)-triene (IV).

By carrying out the reaction according to the invention in the presence of the thiourea/$AlCl_3$ reagent pair and organic solvents, preferably dichloromethane and 1,2-dichloroethane, 3β-hydroxyestra-1,3,5(10)-triene-17-one (V) was also prepared by the demethylation of 3 β-methoxyestra-1,3,5 (10)-triene-17-one (VI).

The invention is further illustrated by the following non-limiting Examples.

EXAMPLE 1

Preparation of 17β-acetoxyestra-1,3,5(10)-triene-3β-ol (111) by Demethylation of 3β-methoxy-17β-acetoxyestra-1,3,5(10)-triene (IV)

To 53.3 g (0.4 mol) of dry aluminium chloride 250 ml of dichloromethane was poured, then 22.84 g (0.3 mol) of crystalline thiourea was added in small portions under stirring over 10 minutes. The addition is carried out at room temperature, at the end the temperature of the mixture raises to 30° C. After stirring the mixture for additional 15 minutes the mixture becomes a transparent olive-drab solution and the temperature returnes to room temperature. Then 32.85 g (0.1 mol) of 3β-methoxy-17β-acetoxyestra-1,3,5(10)-triene of formula (IV) dissolved in 40 ml of dichloromethane is added over 15 minutes raising the reaction temperature to 30° C. The mixture is heated to reflux and is maintained at this temperature for 4 hours under stirring. The reaction proceeds along with gradual precipitation of the product in yellow crystals giving the 17β-acetoxyestra-1,3,5(10)-triene-3-ol of the formula (III) in 65-70% yield. In order to improve the yield and the purity of the product the reaction is continued as follows:

To the reaction mixture 200 ml of 1,1,2,2-tetrachloroethylene is added over 5 minutes. The mixture is kept under continuous stirring and the temperature of the mixture is gradually elevated from 40° C. to 75° C. in such a way that first the dichloromethane being present is distilled off at 40-43° C. After 2-2.5 hours (while 265 ml of dichloromethane is distilled off) the distillation head temperature dropped. At this time the temperature is elevated to 75-80° C. with heating and maintained at this value for 1 hour, then the mixture is cooled to 30° C. and 200 ml of 5 wt % hydrochloric acid is added in small portions while taking care of that the temperature not to exceed 75° C. When the addition of the HCl is finished, the colour of the product changes first from reddish orange to pink and after stirring for additional 30 minutes to white. At this time the reaction mixture is cooled to room temperature, the stirring is stopped and the product is filtered off, washed and dried.

The small amount of hydrogen sulfide formed in the reaction is introduced into a trap containing 10 wt % aqueous sodium hydroxide.

The reaction gives 29.5 g (93.9 %) of 17β-acetoxyestra-1, 3,5(10)-triene-3-ol of the formula (III) as a white powder.

EXAMPLE 2

Preparation of 3β-hydroxyestra-1,3,5(10)-triene-17-one (V) by Demethylation of 3β-methoxyestra-1,3,5 (10)-triene-17-one (VI)

230 mg (3 mmol) of thiourea and 560 mg (4.2 mmol) of aluminium chloride are mixed. To the resulting oily liquid 285 mg (1 mmol) of 3β-methoxyestra-1,3,5(10)-triene-17-one (VI) dissolved in 10 ml of dichloromethane is added. The reaction mixture is stirred for 4 hours under reflux, then 10 ml of 1,2-dichloroethane is added over 5 minutes. The temperature of the reaction mixture is gradually elevated from 40° C. to 75° C. under continuous stirring in such a way that first the dichloromethane being present in the mixture is distilled off at 40-43° C. distillation head temperature. Then the mixture is heated to reflux and maintained at reflux temperature (75-80° C.) for 3 hours. After that the mixture is cooled to room temperature and 5 ml of 5 wt % hydrochloric acid is added in small portions while taking care of that the temperature not to exceed 75° C. When the addition of the HCl is finished, the colour of the product changes first from reddish orange to pink and after stirring for additional 30 minutes to white. At this time the reaction mixture is cooled to room temperature, the stirring is stopped and the product is filtered off, washed and dried.

150 mg (54 %) of 3β-hydroxyestra-1,3,5(10)-triene-17-one of the formula (V) is obtained as a white powder.

EXAMPLE 3

Preparation of Hydroxybenzene by Demethylation of Methoxybenzene

To a mixture of 5.32 g (40 mmol) of aluminium chloride and 1.52 g (20 mmol) of thiourea 2.16 g (20 mmol) of methoxybenzene is added. The reaction mixture is heated to 90° C. and maintained at this temperature for 1 hour. The mixture is then cooled to room temperature and 20 ml of 5 wt % hydrochloric acid is added. The mixture is extracted with chloroform, the organic layer is dried over sodium sulfate and evaporated, yielding 1.79 g (95.2%) of hydroxybenzene.

EXAMPLE 4

Preparation of 2-hydroxynaphthalene by Demethylation of 2-methoxynaphthalene of the Formula (VII)

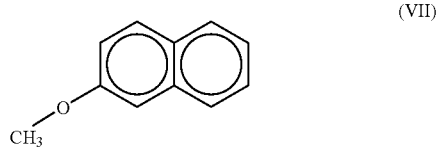

(VII)

To a mixture of 5.32 g (40 mmol) of aluminium chloride and 1.52 g (20 mmol) of thiourea 3.16 g (20 mmol) of 2-methoxynaphtalene of the formula (VII) is added. The reaction mixture is heated to 90° C. and maintained at this temperature for 1 hour. The mixture is then cooled to room temperature and 20 ml of 5 wt % hydrochloric acid is added. The precipitated product is filtered, washed and dried to give 2.58 g (89.5 %) of 2-hydroxynaphthalene.

EXAMPLE 5

Preparation of 1-hydroxy-4-methylbenzene by Demethylation of 1-methoxy-4-methylbenzene The method described in Example 3 is applied with the alteration that instead of methoxybenzene 2.44 g (20 mmol) of 1-methoxy-4-methylbenzene is used.
2.16 g (100%) of 1-hydroxy-4-methylbenzene is obtained.

EXAMPLE 6

Preparation of 1-hydroxy-4-chlorobenzene by Demethylation of 1-methoxy-4-chlorobenzene The method described in Example 3 is applied with the alteration that instead of methoxybenzene 2.85 g (20 mmol) of 1-methoxy-4-chlorobenzene is used.
2.47 g (96%) of 1-hydroxy-4-chlorobenzene is obtained.

EXAMPLE 7

Preparation of 1-hydroxy-2-chlorbenzene by Demethylation of 1-methoxy-2-chlorbenzene The method described in Example 3 is applied with the alteration that instead of methoxybenzene 2.85 g (20 mmol) of 1-methoxy-2-chlorbenzene is used.
2.01 g (78.2%) of 1-hydroxy-2-chlorbenzene is obtained.

EXAMPLE 8

Preparation of 1-hydroxy-2-bromobenzene by Demethylation of 1-methoxy-2-bromobenzene The method described in Example 3 is applied with the alteration that instead of methoxybenzene 3.74 g (20 mmol) of 1-methoxy-2-bromobenzene is used.
3.17 g (91.7%) of 1-hydroxy-2-bromobenzene is obtained.

EXAMPLE 9

Preparation of 1-hydroxy-4-bromobenzene by Demethylation of 1-methoxy-4-bromobenzene The method described in Example 3 is applied with the alteration that instead of methoxybenzene 3.74 g (20 mmol) of 1-methoxy-4-bromobenzene is used.
3.12 g (90.2%) of 1-hydroxy-4-bromobenzene is obtained.

EXAMPLE 10

Preparation of 1-hydroxy-4-fluorobenzene by Demethylation of 1-methoxy-4-fluorobenzene The method described in Example 3 is applied with the alteration that instead of methoxybenzene 2.52 g (20 mmol) of 1-methoxy-4-fluorobenzene is used.
2.15 g (95.8%) of 1-hydroxy-4-fluorobenzene is obtained.

EXAMPLE 11

Preparation of 1-hydroxy-4-nitrobenzene by Demethylation of 1-methoxy-4-nitrobenzene To a mixture of 5.32 g (40 mmol) of aluminium chloride and 1.52 g (20 mmol) of thiourea 1.53 g (10 mmol) of 1-methoxy-4-nitrobenzene is added. The reaction mixture is heated to 40° C. and maintained at this temperature of 2 hours, then cooled to room temperature and 20 ml of 5 wt % hydrochloric acid is added. The precipitated product is filtered, washed and dried giving 1.13 g (81.2%) of 1-hydroxy-4-nitrobenzene.

EXAMPLE 12

Preparation of Hydroxybenzene by Desethylation of Ethoxybenzene

The method described in Example 3 is applied with the alteration that instead of methoxybenzene 2.44 g (20 mmol) of ethoxybenzene is used.
1.77 g (94.3%) hydroxybenzene is obtained.

EXAMPLE 13

Preparation of Hydroxybenzene by Debutylation of n-butoxybenzene

To a mixture of 2.66 g (20 mmol) of aluminium chloride and 0.76 g (10 mmol) of thiourea 1.50 g (10 mmol) of n-butoxybenzene is added. The reaction mixture is heated to 90° C. and maintained at this temperature for 3 hours. The mixture is cooled to room temperature and 20 ml of 5 wt % hydrochloric acid is added. The mixture is stirred for a few minutes, the phases are separated. The aqueous phase is extracted with 20 ml of dichloromethane. The combined dichloromethane phases are washed with 3×10 ml of 5% aqueous sodium hydroxide. The combined alkaline phases are acidified with 18 wt % hydrochloric acid and extracted with 3×10 ml of dichloromethane. The combined dichloromethane phases are washed with water, dried over sodium sulfate and evaporated to give 0.59 g (62.8%) of hydroxybenzene.

EXAMPLE 14

Preparation of 1,4-dihydroxybenzene by Desethylation 1-hydroxy-4-ethoxybenzene To a mixture of 2.66 g (20 mmol) of aluminum chloride and 0.76 g (10 mmol) of thiourea 1.38 g (10 mmol) of 1-hydroxy-4-ethoxybenzene is added. The reaction mixture is heated to 90° C. and maintained at this temperature for 3 hours. Then 10 ml of 1,1,2,2-tetrachloroethylene is added and stirring is continued for an additional 1.5 hour at the same temperature. The mixture is then cooled to room temperature and 20 ml of 5 wt % hydrochloric acid is added.

The mixture is stirred for a few minutes, then the phases are separated. The aqueous phase is extracted with 10 ml of dichloromethane. To the aqueous layer so obtained 30 ml of ethanol is added, the mixture is concentrated to 5 ml volume and the product precipitates on standing after 2 days yielding 0.27 g (24.5%) of 1,4-dihydroxybenzene.

EXAMPLE 15

Preparation of 2-hydroxybenzoic acid by Demethylation of 1-carboxy-2-methoxybenzene The method described in Example 4 is applied with the alteration that instead of 2-methoxynaphthalene 3.04 g (20 mmol) of 1-carboxy-2-methoxybenzene is used yielding 2.48 g (89.9%) of 2-hydroxybenzoic acid.

EXAMPLE 16

Preparation of 4-hydroxybenzoic Acid by Desethylation of 1-carboxy-4-ethoxybenzene The method described in Example 4 is applied with the alteration that instead of 2-methoxynaphthalene 3.32 g (20 mmol) of 1-carboxy-4-ethoxybenzene is used yielding 1.86 g (61.2%) of 4-hydroxybenzoic acid.

EXAMPLE 17

Preparation of 5,6,7,8-tetrahydro-2-naphthol by Demethylation of 5,6,7,8-tetrahydro-2-methoxynaphthalene of the Formula (VIII)

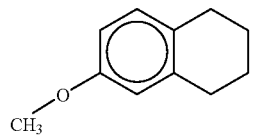

(VIII)

To a mixture of 5.67 g (42.5 mmol) of aluminium chloride and 2.28 g (30 mmol) of thiourea 1.62 g (10 mmol) of 5,6,7,8-tetrahydro-2-methoxynaphthalene is added. The reaction mixture is heated to 90° C. and maintained at this temperature for 1 hour, then cooled to room temperature, 20 ml of 1,2-dichloroethane is added and the mixture is poured onto 20 ml of 5 wt % hydrochloric acid/ice mixture.

The mixture is stirred for a few minutes, then the phases are separated. The aqueous layer is extracted with 20 ml of 1,2-dichloroethane. The combined dichloroethane phases are washed with 3×10 ml of 5% aqueous sodium hydroxide. The combined alkaline phases are acidified with 18 wt % hydrochloric acid solution, then extracted with 3×10 ml of dichloromethane. The combined dichloromethane phases are washed with water, dried over sodium sulfate and evaporated yielding 0.85 g (57.4) of 5,6,7,8-tetrahydro-2-naphthol.

EXAMPLE 18

Preparation of 1-oxo-1,2,3,4-tetrahydro-6-hydroxynaphthalene by Demethylation of 1-oxo-1,2,3,4-tetrahydro-6-methoxynaphthalene of the Formula (IX)

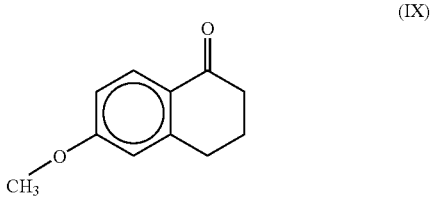

(IX)

To a mixture of 5.67 g (42.5 mmol) of aluminium chloride and 2.28 g (30 mmol) of thiourea 1.76 g (10 mmol) of 1-oxo-1,2,3,4-tetrahydro-6-methoxynaphthalene is added. The reaction mixture is heated to 90° C., maintained at this temperature for 3 hours, then cooled to room temperature and 20 ml of 1,2-dichloroethane is added. The mixture is poured to 20 ml of 5 wt % hydrochloric acid and is stirred at 50° C. for 1 hour.

The mixture is cooled to room temperature, the phases are separated and the aqueous layer is extracted with 20 ml of 1,2-dichloroethane. The combined dichloroethane phases are washed with 3×10 ml of 5 wt % aqueous sodium hydroxide solution. The alkaline phases are combined, acidified with 18 wt % hydrochloric acid solution and extracted with 3×10 ml of dichloromethane. The combined dichloromethane phases are washed with water, dried over sodium sulfate and evaporated yielding 0.63 g (38.8%) of 1-oxo-1,2,3,4-tetrahydro-6-hydroxynaphthalene.

EXAMPLE 19

Peparation of a Mixture of 3-hydroxy-4-methoxyacetophenone (X) and 4-hydroxy-3-methoxyacetophenone (XI) Obtained in 1:1 Molar Ratio by Demethylation of 3,4-dimethoxyacetophenone (XII)

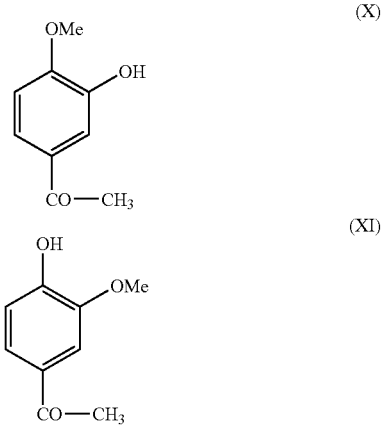

(X)

(XI)

-continued

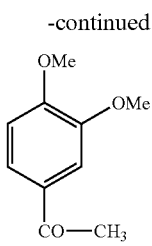

(XII)

1.06 g (8 mmol) of aluminium chloride and 300 mg (4 mmol) of thiourea are mixed, the resulting oily liquid is dissolved in 10 ml of dichloromethane. To this solution 0.36 g (2 mmol) of 3,4-dimethoxyacetophenone (XII) dissolved in 5 ml of dichloromethane is added. The reaction mixture is stirred under reflux for 5 hours, then cooled to room temperature and 5 ml of 5 wt % hydrochloric acid is added.

The mixture is stirred for a few minutes, the phases are separated and the aqueous layer is extracted with 2 x 5 ml of dichloromethane. The combined organic phases are washed with 3×10 ml of 5 wt % aqueous sodium hydroxide solution. The alkaline phases are combined, acidified with 18 wt % hydrochloric acid solution and extracted with 3×10 ml of dichloromethane. The combined dichloromethane phases are washed with water, dried over sodium sulfate and evaporated.

0.12 g oil is obtained which solidifies on standing, consisting of 3-hydroxy-4-methoxyacetophenone (X) and 4-hydroxy-3-methoxyacetophenone (XI) in 1:1 molar ratio (yield: 40%).

The invention claimed is:

1. A process for the preparation of a phenolic hydroxy-substituted compound of the general formula (I) by desalkylation of an alkyl aryl ether of the general formula (II),

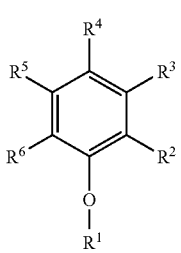

(I)

(II)

in said general formulae $R^1$ stands for straight chain or branched $C_{1-6}$ alkyl group; $R^2$, $R^3$, $R^4$, $R^5$, and $R^6$ have the same or different meanings and stand for hydrogen or halogen atom, hydroxy, carboxy, nitro, oxo, $C_{1-6}$ alkylcarbonyl, straight chain or branched alkyl or —alkoxy, or aryl group, or $R^3$ and $R^4$ together stand for a 5-7 membered ring or fused ring system; said 5-7 membered ring may be a partially saturated ring optionally substituted with an oxo group or can be an unsaturated ring;

or said fused ring system may constitute with the first ring a steroid, characterized in that desalkylation is carried out with the use of a thiourea/aluminum chloride reagent pair.

2. A process according to claim 1, characterized in that the thiourea and the aluminum chloride is applied in a molar ratio from 1:1 to 1:4 in the thiourea/aluminium chloride reagent pair.

3. A process according to claim 1, characterized in that the thiourea and the aluminum chloride is applied in a molar ratio from 1:1 to 1:2 in the thiourea/aluminium chloride reagent pair.

4. A process according to claim 1, characterized in that in the starting alkyl aryl ethers of the general formula (II) $R^1$ stands for methyl, ethyl, n-propyl or n-butyl group.

5. A process according to claim 1, characterized in that the reaction is carried out in the presence of one or more organic solvents or in the absence of a solvent.

6. A process according to claim 5, characterized in that dichloromethane, 1,2-dichloroethane, chloroform, benzene, toluene, xylene, 1,1,2,2-tetrachloroethane, 1,1,2,2-tetrachloroethylene is used as organic solvent.

7. A process according to claim 1, characterized in that the thiourea present in the thiourea/aluminium chloride reagent pair is used in 1-5 mole equivalent amount per one ether group to be desalkylated present in an alkyl aryl ether of the general formula (II).

8. A process according to claim 1, characterized in that the aluminum chloride present in the thiourea/aluminium chloride reagent pair is used in 1-20 mole equivalent amount per one ether group to be desalkylated present in an alkyl aryl ether of the general formula (II).

9. A process according to claim 1, characterized in that the desalkylation is carried out at a temperature ranging from 0° C. to 130° C.

10. A process according to claim 1, characterized in that the aluminum chloride present in the thiourea/aluminium chloride reagent pair is used in 1-20 mole equivalent amount per one ether group to be desalkylated present in an alkyl aryl ether of the general formula (II) and the desalkylation is carried out at a temperature ranging from 0° C. to 130° C.

11. A process according to claim 1, wherein said fused ring system constitutes with the first ring an estratriene derivative optionally substituted with an oxo or $C_{1-4}$ alkylcarbonyloxy group in the 17 position.

12. A process according to claim 1 for the preparation of 17β-acetoxyestra-1,3,5(10)triene-3-ol of the formula (III)

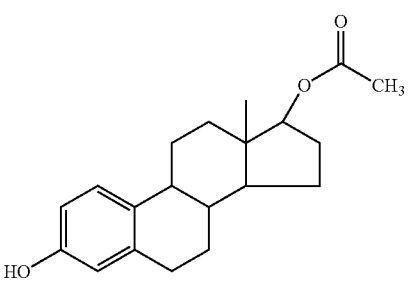

(III)

by demethylation of 3β-methoxy-17β-acetoxyestra-1,3,5 (10)-triene of formula (IV),

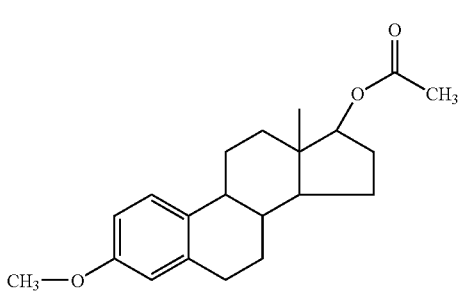

(IV)

characterized in that the demethylation is carried out by using thiourea/aluminium chloride reagent pair in the presence of organic solvents.

13. A process according to claim 1 for the preparation of 3β-hydroxyestra-1,3,5(10)triene-17-one of the formula (V)

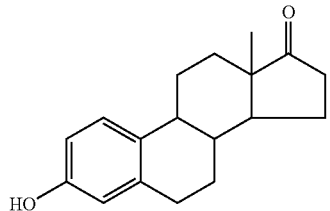
(V)

by demethylation of 3β-methoxyestra-1,3,5(10)triene-17-one of the formula (VI),

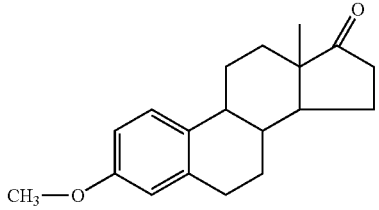
(VI)

characterized in that the demethylation is carried out by using thiourea/aluminium chloride reagent pair in the presence of organic solvents.

* * * * *